(12) United States Patent
Del Rio

(10) Patent No.: US 7,527,486 B2
(45) Date of Patent: May 5, 2009

(54) SURGICAL PNEUMATIC MOTOR FOR USE WITH MRI

(75) Inventor: Eddy H. Del Rio, Royal Palm Beach, FL (US)

(73) Assignee: The Anspach Effort, Inc, Palm Beach Gardens, FL (US)

( * ) Notice: Subject to any disclaimer, the term of this patent is extended or adjusted under 35 U.S.C. 154(b) by 316 days.

(21) Appl. No.: 11/074,821

(22) Filed: Mar. 8, 2005

(65) Prior Publication Data
US 2005/0245913 A1 Nov. 3, 2005

Related U.S. Application Data

(60) Provisional application No. 60/567,189, filed on Apr. 30, 2004, provisional application No. 60/567,188, filed on Apr. 30, 2004.

(51) Int. Cl.
F01C 21/00 (2006.01)
F03C 2/00 (2006.01)
F04C 15/00 (2006.01)

(52) U.S. Cl. .................. 418/270; 418/15; 418/82; 418/104; 418/140; 418/159; 418/153; 418/179; 418/259; 418/268

(58) Field of Classification Search ............ 418/15, 418/82, 104, 149, 180, 259, 266–268, 270, 418/140, 152–153, 159, 179
See application file for complete search history.

(56) References Cited

U.S. PATENT DOCUMENTS

| 3,734,652 | A | * | 5/1973 | Barnett | 418/270 |
| 3,827,834 | A | * | 8/1974 | Kakimoto | 418/15 |
| 4,799,867 | A | * | 1/1989 | Sakamaki et al. | 418/1 |
| 5,954,141 | A | * | 9/1999 | Li et al. | 173/93.5 |
| 6,589,033 | B1 | * | 7/2003 | Johnson et al. | 418/179 |

* cited by examiner

Primary Examiner—Theresa Trieu
(74) Attorney, Agent, or Firm—Norman Friedland

(57) ABSTRACT

A surgical pneumatic motor is designed to be used with or without an MRI machine without affecting or influencing the magnetic characteristic of the MRI machine. The motor includes an improved vane motor with undercuts in the spindle to increase the power faces of the vanes and spindle itself, the holes in the cylinder are modified to increase the sealing area between the spindle. The inlet cylindrical holes and the cylinder holes and grooves are arranged to enhance the life . Wear of the edge of the vanes is decreased by the judicious location of the discharge holes. The bearings are cooled by bypassing a portion of cylinder air before re-entering the air. The noise is attenuated by a cris-cross plug in the hose the temperature of the handle is reduced by a serrated sleeve. Slipping discs in the seal serves to enhance seal life.

28 Claims, 13 Drawing Sheets

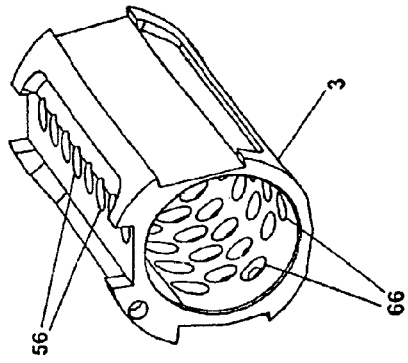
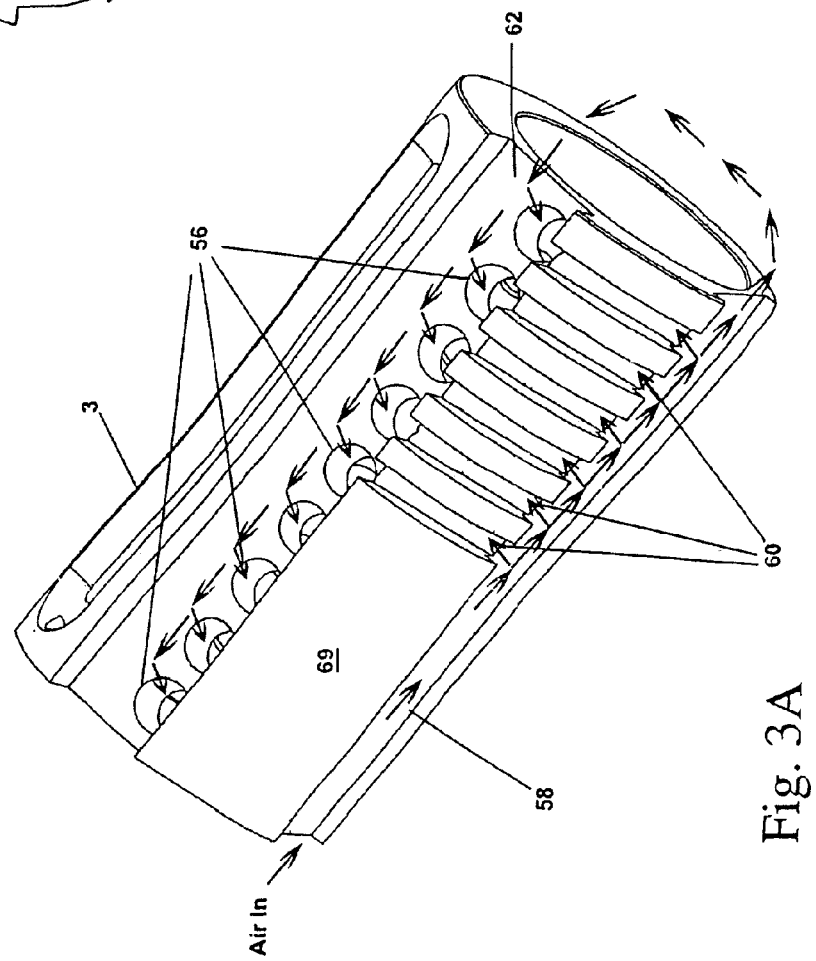

Vane Motion

Vane Contact Area over Holes

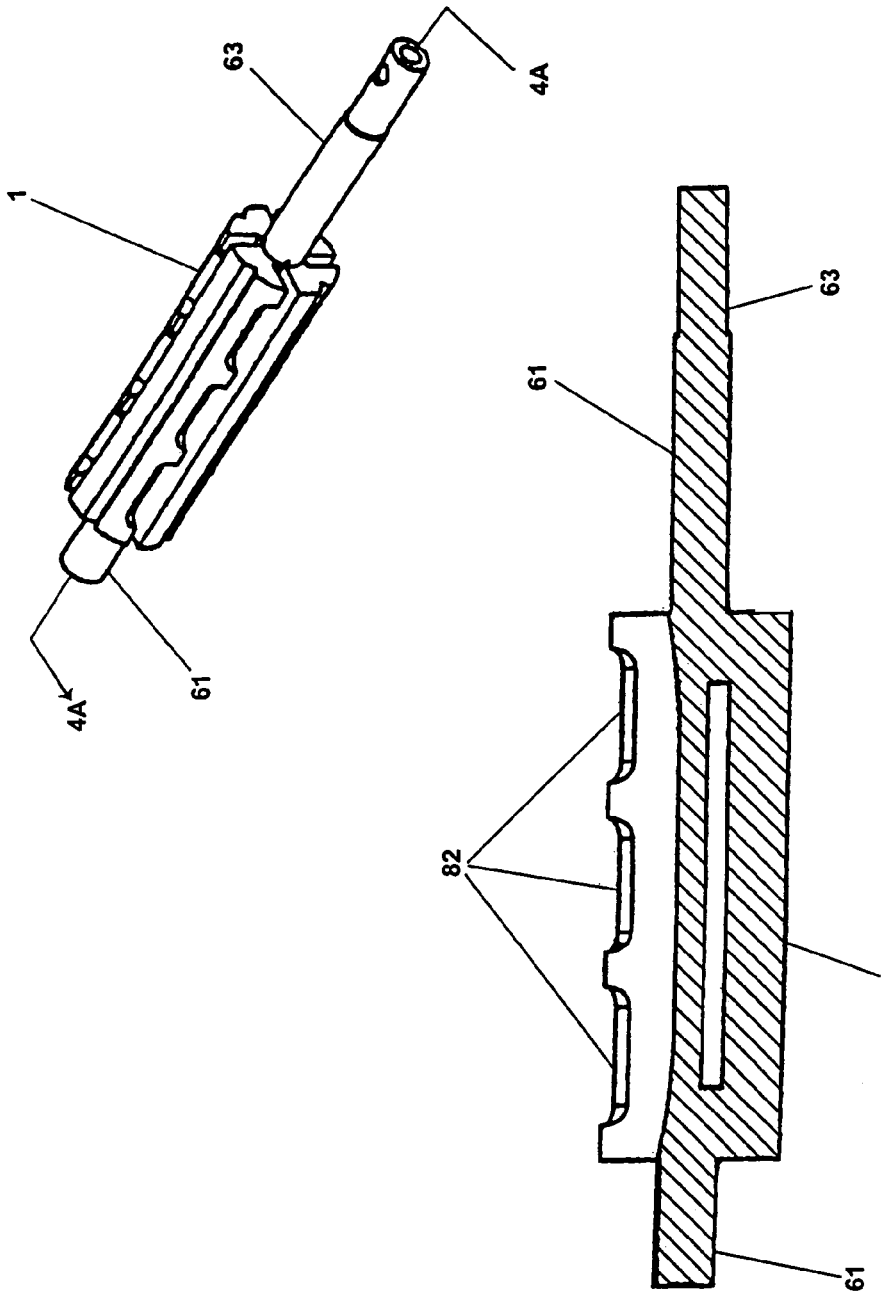

SURGICAL PNEUMATIC MOTOR FOR USE WITH MRI

This application claims the benefits under 35 U.S.C. § 119(e) of the U.S. provisional patent application 60/567,189 filed on Apr. 30, 2004.

CROSS REFERENCES

This application relates to the subject matter described in provisional patent application 60/567,188 filed on Apr. 30, 2004 . This invention also relates to U. S. patent application Ser. No. 10/306,256 filed on Nov. 27, 2002 entitled NEEDLE/ROLLER BEARING by Thomas E. Anspach and myself and identified as. Both of these applications are commonly assigned to The Anspach Effort, Inc and are incorporated herein by reference.

FEDERALLY SPONSORED RESEARCH

None.

TECHNICAL FIELD

This invention relates to pneumatic motors for use by surgeons for performing surgical procedures that are typical in general surgery, neurosurgery, endoscopic, arthroscopic and the like and more particularly to an improved pneumatic motor that has utility in connection with an MRI process.

BACKGROUND OF THE INVENTION

As one skilled in the medical field appreciates, it is unacceptable to use any medical instrument that would interfere with the magnetic field of a magnetic resonance imaging machine (MRI). As is well known, the MRI utilizes an external magnetic field that is created by a series of electromagnets in a scanner that serve to excite the hydrogen atoms in the body of the patient being analyzed. These hydrogen atoms create radio signals which are read by a computer and converted into detailed images. This invention addresses this problem by providing a pneumatic motor that is capable of being used in the presence of an MRI machine without adversely affecting the magnetic field generated thereby and hence, is incapable of adversely affecting the image generated by this machine. In addition, as will be more fully explained hereinbelow, this invention also provides improvements to heretofore known pneumatic surgical motors notwithstanding the fact that these prior art motors are not usable in an MRI environment. In other words, this invention applies to pneumatic surgical motors that can be used with MRI machines and to those motors that cannot be used with MRI machines. Obviously, a motor that can be used with an MRI machine can also be used where an MRI machine is not being used.

This invention contemplates the improvement of heretofore known pneumatic surgical motors including the pneumatic surgical motors being manufactured by and sold by the assignee and all are well known in the medical industry as the Black Max, the Micro Max and the Micro Max Plus and all of which are incorporated herein by reference. While these motors mentioned immediately above in this paragraph are not capable of use with MRI machines, this invention provides all of the features that are associated with these motors, but does so with an improved surgical instrument. For example, the Black Max is a heavy duty motor that is more powerful and larger than the other two motors, but is heavier, hotter, noisier and vibrates more than these other motors. The Micro Max, supra, was developed to reduce the size, noise, vibration and heat and to be essentially more gentle for use by the surgeon and likewise, has developed a niche in the industry. Obviously, the power is reduced. However, this motor for some medical procedures does not meet the needs of the surgeons because it lacked the necessary power which gave rise to the Micro Max Plus motor, which, again, has more power than the Micro Max but, yet, less power than the Black Max. The Micro Max Plus falls in the category of being more gentle for use by the surgeon but again, because of the increased power, heat, vibrations and weight of the Micro Max Plus (higher than the Micro Max but still lower than the Black Max) it, likewise, has gained a niche in the industry. A more technical way of looking at each of these motors is that the length of the cylinder supporting the vanes of the each of the motors are increased as a function of the power generated, namely, the lengths of the cylinders of the Black Max=1.0 inch ("), the Micro Max=¾" and the Micro Max Plus=½". It is reasonable to state that each of these motors served a particular need for a particular surgeon doing a particular operation or medical procedure on a patient.

As one skilled in this technology will appreciate, the outside diameter of all of the well known commercially available pneumatic surgical motors including the ones noted in the above paragraphs are substantially equal and include a rotor that is driven by pressurized air for rotating a spindle that is rotatably supported by bearings in an outer housing that serves as the handle of the motor. All of these motors also include in some form or another the necessary seals, anti-rotational device, inlet and outlet for the pressurized air and means for lubricating the bearings and their support structures or internal housings.

We have found that we can provide an improved pneumatic surgical motor that satisfies the requirements of all the functions of the three motors that are discussed in the above paragraphs, but is an improvement there over while providing higher power with a smaller cylinder than the one in the Black Max, is lighter than the smallest of these motors, is cooler, exhibits less vibrations, is quieter and is as gentle to handle as is the smallest of these three motors. These improvements are not only germane to the motors manufactured by the assignee, but are improvements to heretofore known competitive motors.

The following aspects of this invention to be discussed immediately below which are not to be construed as limitations thereto, contribute to the overall improvements to the inventive motor. . . .

1. Utilize spindle bearings with alternating metal and plastic needles.
2. Zero velocity axial thrust support for minimizing wear and lower heat.
3. Laminated seal for lower velocity and lower heat.
4. Increased vane working surface for augmenting the power of the motor.
5. Angled slots formed on the spindle to enhance power of the motor and minimizes wear by discretely.
6. Spindle end thrust bearings to prevent metal-to-metal on outward exerted axial thrust.
7. Exhaust holes formed on the cylinder discharging compressed air are judiciously located to minimize wear on the edge of the vane by distributing contact area evenly and to reduce noise of the motor.
8. Cylindrical holes for the input air to the vane motor so as to increase air volume.

9. Cylinder crescent seal to increase the effectiveness of the spindle-to-cylinder gap seal and minimize lubrication requirements.
10. Stainless steel housing and isolation peek sleeve.
11. Increased power cycle by increasing the circumferential spacing between the vane motor's inlet and outlet ports.
12. Noise reduction by crisscrossing outlet air flow.
13. Slots in the cylinder formed adjacent to the inlet holes for directing air cool over the cylinder before entering the vane motor.

SUMMARY OF THE INVENTION

An object of this invention is to provide a surgical motor for powering drills, burrs and the like for use in surgical procedure where an MRI machine is being utilized and an improved surgical motor.

Another object of this invention is to provide an improved surgical motor characterized as having spindle bearings with alternating metal and plastic needles, zero velocity axial thrust support for minimizing wear and lower heat, laminated seal for lower velocity and lower heat, increased vane working surface for augmenting the power of the motor, angled slots formed on the spindle to enhance power of the motor and minimizes wear by discretely, spindle end thrust bearings to prevent metal-to-metal on outward exerted axial thrust, exhaust holes formed on the cylinder discharging compressed air are judiciously located to minimize wear on the edge of the vane by distributing contact area evenly and to reduce noise of the motor, cylindrical holes for the input air to the vane motor so as to increase air volume, cylinder crescent seal to increase the effectiveness of the spindle-to-cylinder gap seal and minimize lubrication requirements, stainless steel housing and isolation peek sleeve, increased power cycle by increasing the circumferential spacing between the vane motor's inlet and outlet ports, noise reduction by crisscrossing outlet air flow, slots in the cylinder formed adjacent to the inlet holes for directing air cool over the cylinder before entering the vane motor.

The foregoing and other features of the present invention will become more apparent from the following description and accompanying drawings.

BRIEF DESCRIPTION OF THE DRAWINGS

These figures merely serve to further clarify and illustrate the present invention and are not intended to limit the scope thereof.

FIG. 3 is a perspective view of the cylinder of the vane motor of this invention;

FIG. 3A is an enlarged perspective view in elevation showing the details of the cooling slots of the cylinder depicted in FIG. 3;

FIG. 4 is a perspective view of the spindle of the vane motor depicted in FIGS. 1 and 2;

FIG. 4A is a sectional view taken along the longitudinal axis lines 4A-4A of the spindle depicted in FIG. 4;

DETAILED DESCRIPTION OF THE INVENTION

While in its preferred embodiment this invention is usable with an MRI machine without jeopardizing the magnetism associated with this machine, it will be appreciated by one skilled in this art that this invention can be utilized in other environment and where it is not intended to be used for MRI applications, it could be fabricated from different materials which typically would be less expensive or have other advantages.

Figure 1:
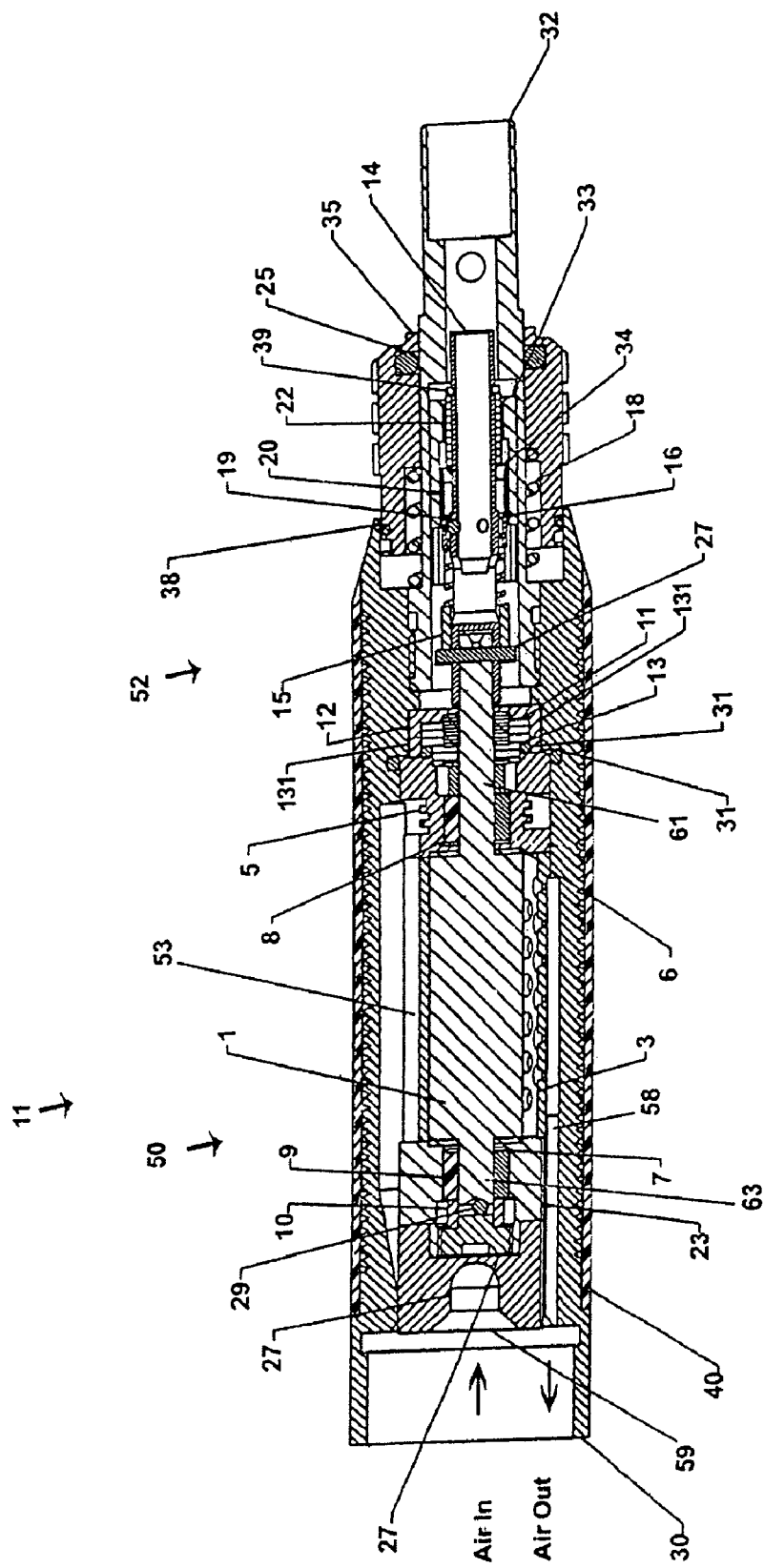
FIG. 1 is a longitudinal cut away sectional view showing the details of the motor of this invention and the chuck mechanism for attaching drill bits and various attachment assemblies.
Figure 2:
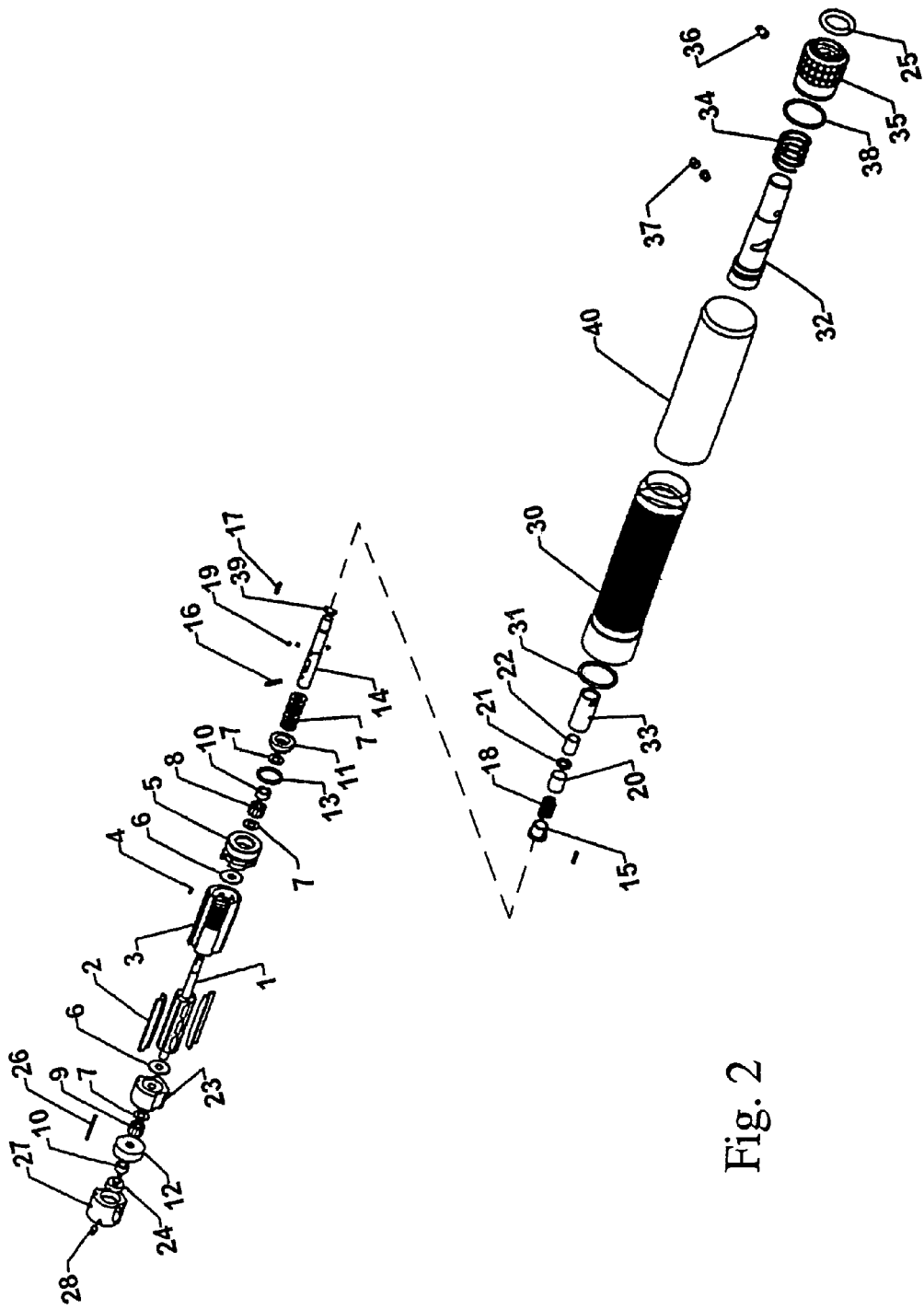
FIG. 2 is an exploded view illustrating the details of this invention.
Figure 5:
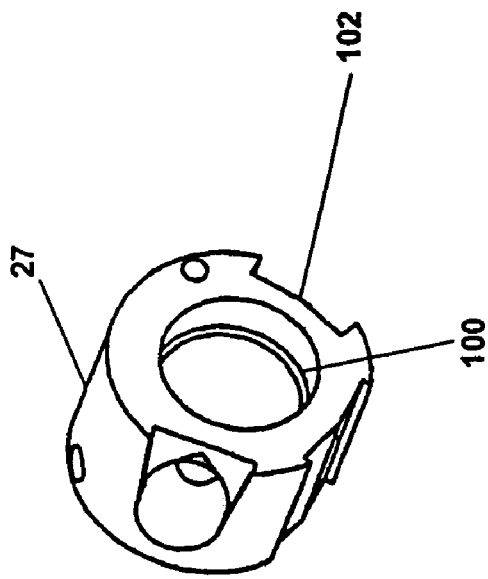
FIG. 5 is a perspective view of the motor adapter depicted in FIGS. 1 and 2.

A better understanding of this invention can be had by referring to FIGS. 1 and 2 which show the motor generally indicated by reference numeral 50 and the attachment mechanism which is generally illustrated by reference numeral 52 including chuck means for removably attaching the attachment and for removably attaching the drill bit, burr and the various surgical instruments used with the motor (not shown). Inasmuch as the elements in the attachment mechanism 52 are well known for the sake of simplicity and convenience the details thereof are omitted hear from and for further details reference should be made to the Black Max, the Micro Max and the Micro Max Plus surgical motors. The surgical motor of this invention comprises spindle 1, vane 2, motor cylinder 3, pin 4, bearing housing 5, thrust washer 6, small Teflon seal 7, pin 8, torlon pin 9, pin retainer 10, seal housing 11, seal housing cap 12, O-ring 13, spindle extension 14, safety spacer 15, small pin 16, safety pin 17, spring 18, retaining ball 19, key ring 20, key ring cap 21, bearing spacer 22, back plate bearing 23, bearing adjusting screw 24, O-ring 25, Pin 26, motor adapter 27, dowel pin 28, ceramic ball 29, motor housing 30, O-ring 31, tube housing 32, lock spacer 33, set screw 34, housing pin 37, O-ring 38, snap ring 39 and sleeve 40.

Power is developed by the vane motor generally illustrated by reference numeral 53 as comprising cylinder 3 and spindle 1. The spindle having diametrically opposed stud shafts 61 and 63 extending on opposite ends thereof and supported by suitable bearings (5,23) carries a plurality of vanes 2 spaced around the circumference and the cylinder 3 includes a plurality of inlet holes and discharge holes that direct pressurized air into the interior of cylinder 3 to impinge on the vanes so as to rotate the spindle for driving the output shaft and judiciously discharging the exhaust air as will be described in detail herein below. First consider the motor cylinder 3 made from a non-magnetic stainless steel material, such as 316 SST and which is a cylindrical element with a single row of a plurality of spindle inlet holes 56 that are axially spaced and which receives the pressurized air through a central inlet opening 59 that flows the air toward the inner surface of the housing 30 into the axial slot 58. As seen in this view the rear or aft end of the motor is on the left hand side and the fore end of the motor is on the right hand side. A plurality of axially spaced circumferential slots or grooves 60 are formed on the fore end of cylinder 3 immediate forward of the blocked off portion 69. A portion of the inlet air from the axial slot 58 flows past portion 69 and flows circumferentially through the grooves 60 and dumps into the spindle inlet holes 56 and the remaining portion of air continues to flow toward the fore end of cylinder 3 and is then directed to be reversed through the axial slot 62. The remaining portion of pressurized inlet air is directed into the plurality of spindle inlet holes 56. It will be noted that spindle inlet holes are drilled holes and cylindrical in shape and are not slots as is the heretofore accepted method of providing inlet openings to the spindle.

As is apparent from the foregoing, the air flowing through the circumferential slots 60 serve to cool the cylinder and the portion of air flowing past the cylinder 3 and back into the cylinder serve to cool the bearings which will be described in further detail hereinbelow. As noted in FIG. 3B the exhaust air flowing out of holes 66 is directed toward the rear of the motor, i.e. toward the left end as viewed in this FIG. 3B and then discharged out of cylinder 3 as will be detailed in the description to follow.

Figure 3B:
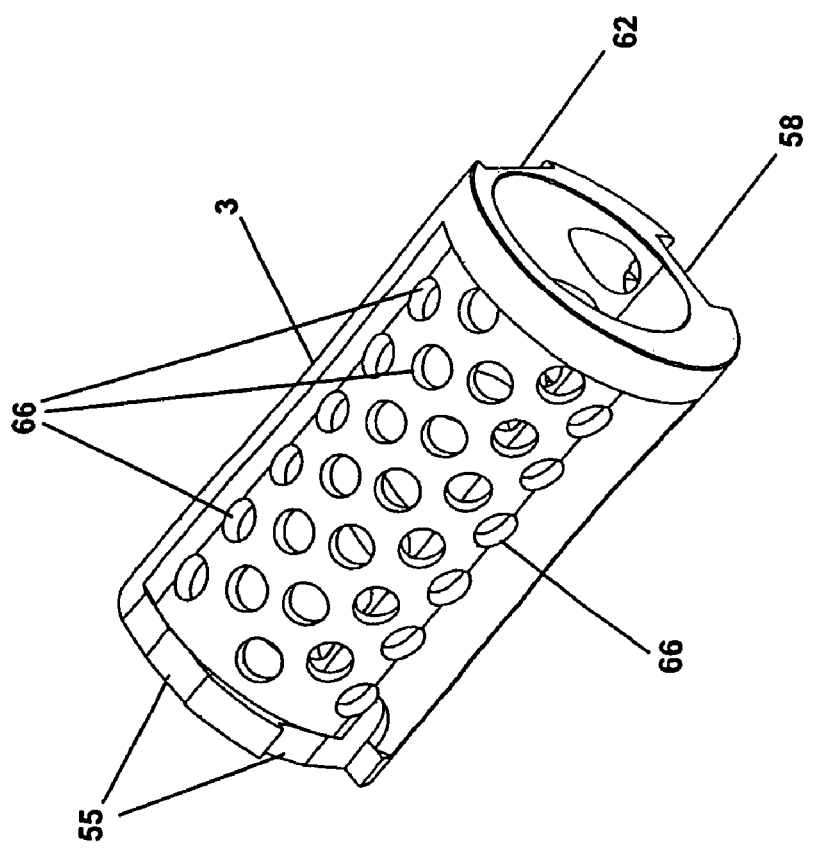
FIG. 3B is a an enlarged perspective view in elevation showing the details of the discharge slots of the cylinder depicted in FIG. 3.
Figure 3C:
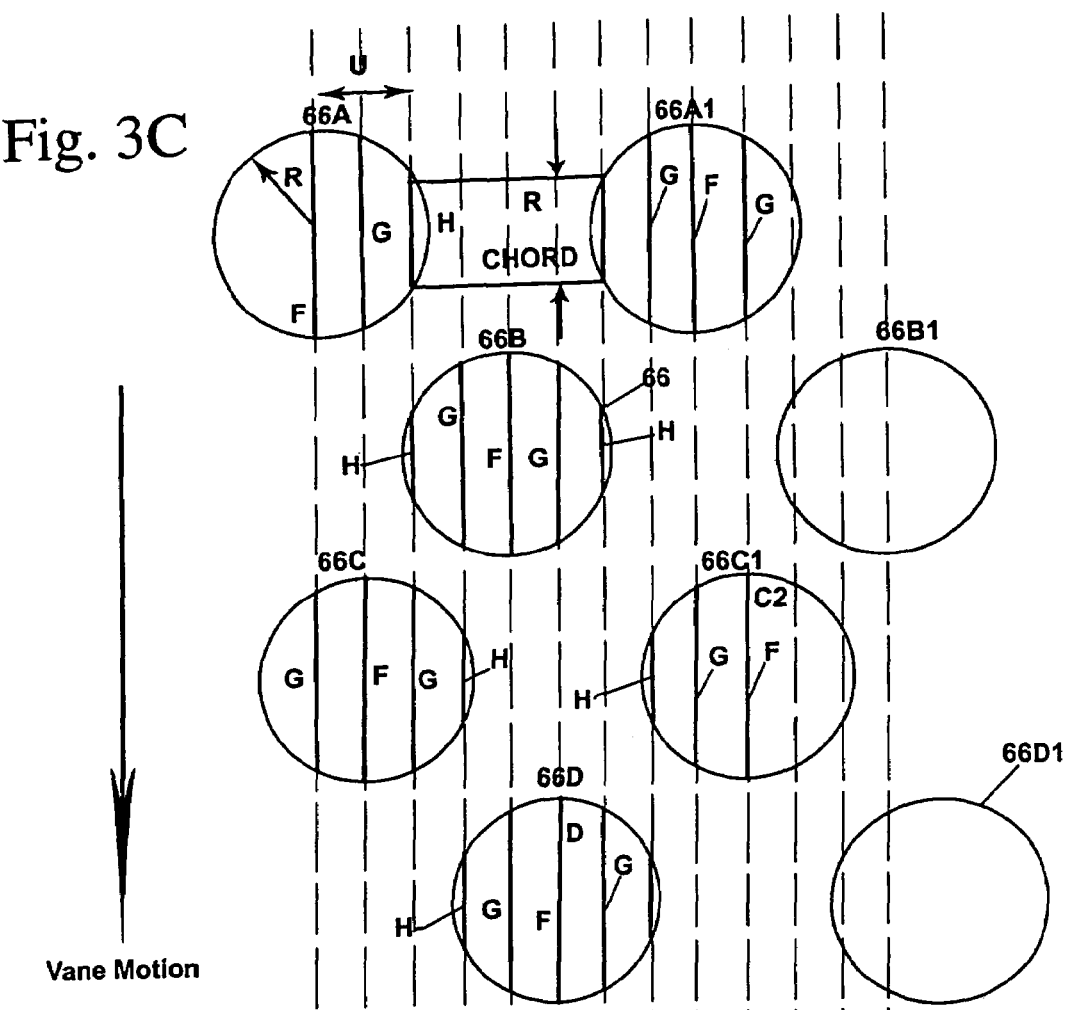
FIG. 3C is a schematic illustration of the orientation of the discharge holes formed in the cylinder depicted in FIG. 3B and illustrating its pattern as the vane displaces over the cylinder surface and holes.
Figure 10:
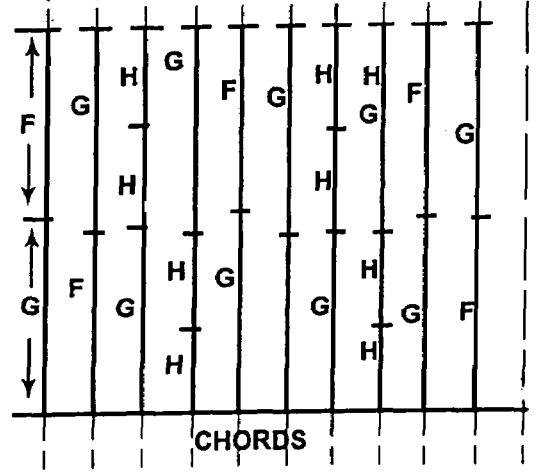
FIG. 10 is a graph illustrating the contact characteristics of the vane passing over the exhaust ports of the cylinder of the vane motor depicted in FIGS. 1 and 2 and its position is in relationship to FIG. 3A.

FIG. 3B illustrates the discharge holes 66 judiciously disposed in cylinder 3 and serve as the exhaust outlet for spindle 1. These holes are arranged so that the vane passing there under will virtually see an even contact of the cylinder surface so as to eliminate the uneven wearing of the vane's outer edge. Because of the arrangement of the discharge ports in heretofore known surgical motors, there exhibited an unevenness of wear on the outer edge of the vanes. To avoid this unevenness as is illustrated in FIG. 3C the column of holes 66 identified as 66A, 66A1, 66B, 66B1, 66C, 66C1, 66D and 66D1, for each repeat in the pattern of holes the relative location of holes A and B is such that a unit of measure U is established for one hole and used to position all the other holes. Referring to hole 66A in FIG. 3C, the cord H at the right hand side is selected and it equals the radius R. The distance between the center line of hole 66A and this cord H establishes the unit U (the unit of measurement) which is used for the measurement to set the relative distance of all other cords within a column. Each space between cords (vertical lines) equals ½ the unit of measurement U. The spacing of rows is not critical save that the adjacent hole in a given row that does not overlap the adjacent hole. The hole 66B is established by aligning chords H of 66B with chords H of 66A and 66A1. The next row 66C is established by aligning the chord G with the centerline F of 66A. Row 66C1 is established by aligning centerline F of 66C1 with chord G of 66A1. With this pattern of holes, each of the vanes 2 will displace uniformly over the surface of the cylinder 3 as shown in FIG. 10. Referring to FIG. 10 showing one repeat of the hole pattern, it will be noted that the displacement of the first two chords over the holes 66A and 66C is equal to F and G. The next displacement over the holes 66A and 66C is equal to G and F. The next displacement of vane 2 is over the holes in 66A, 66B and 66C and this is equal to chords H, H and G. By following this pattern throughout the displacement of the vanes it will be noted that the total distance and hence, area that the edge of the vane is in contact with each of the holes of the cylinder is equal. It then follows that the total average area of contact that the edge of the vane relative to the surface of the cylinder is also equal. By designing the hole pattern of the cylinder in this manner, the vanes will wear evenly throughout its cycle and hence, will evidence a longer life.

Figure 4B:
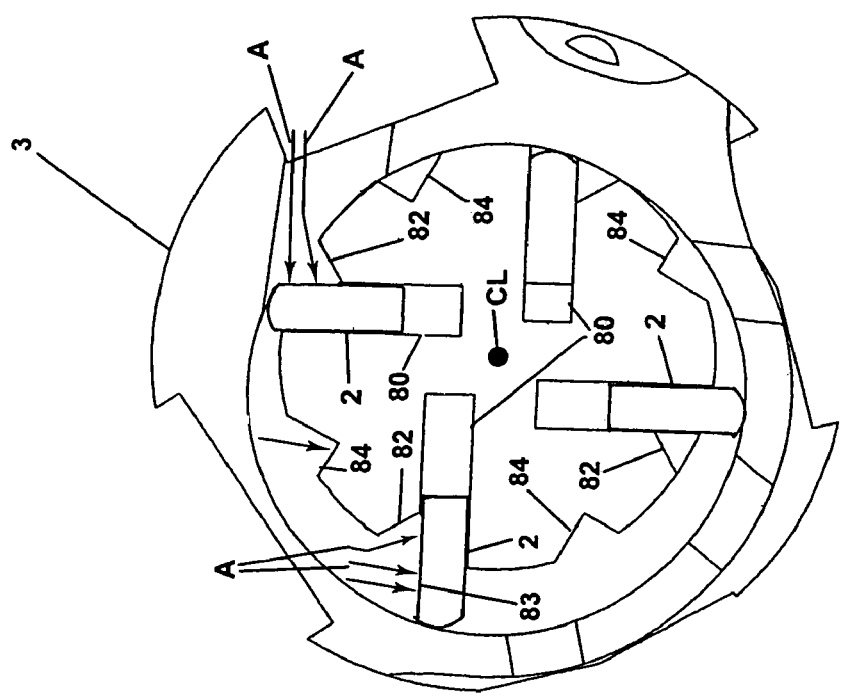
FIG. 4B is a view taken along the lateral axis 4B-4B showing the increased working area of the air flow acting on the vane and spindle depicted in FIG. 4.
Figure 4C:
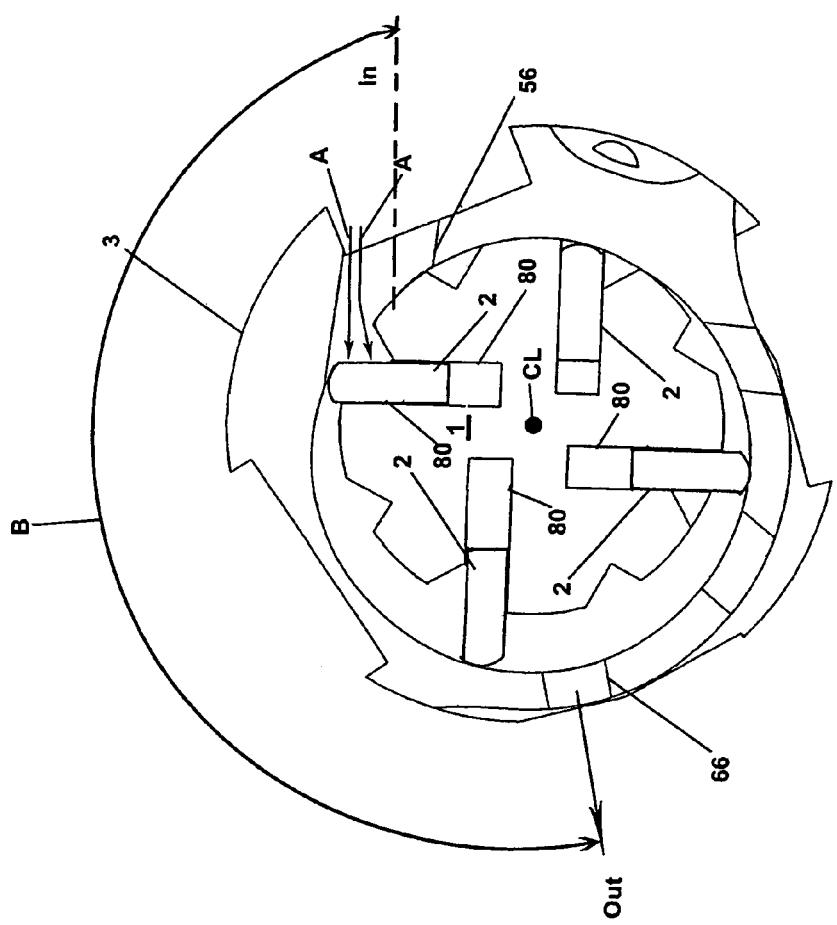
FIG. 4C is a view identical to the view depicted in FIG. 4B illustrating the increased displacement of the vane to increase the power of the vane motor.
Figure 4D:
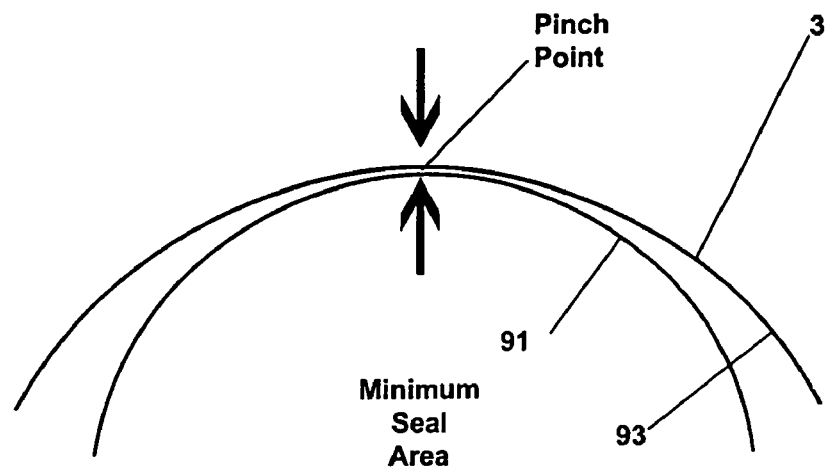
FIG. 4D is a schematic illustration of the relationship of the outer diameter of the spindle to the inner diameter of the cylinder showing a tangent point of contact and an enlarged portion to define a crescent seal.
Figure 4D:
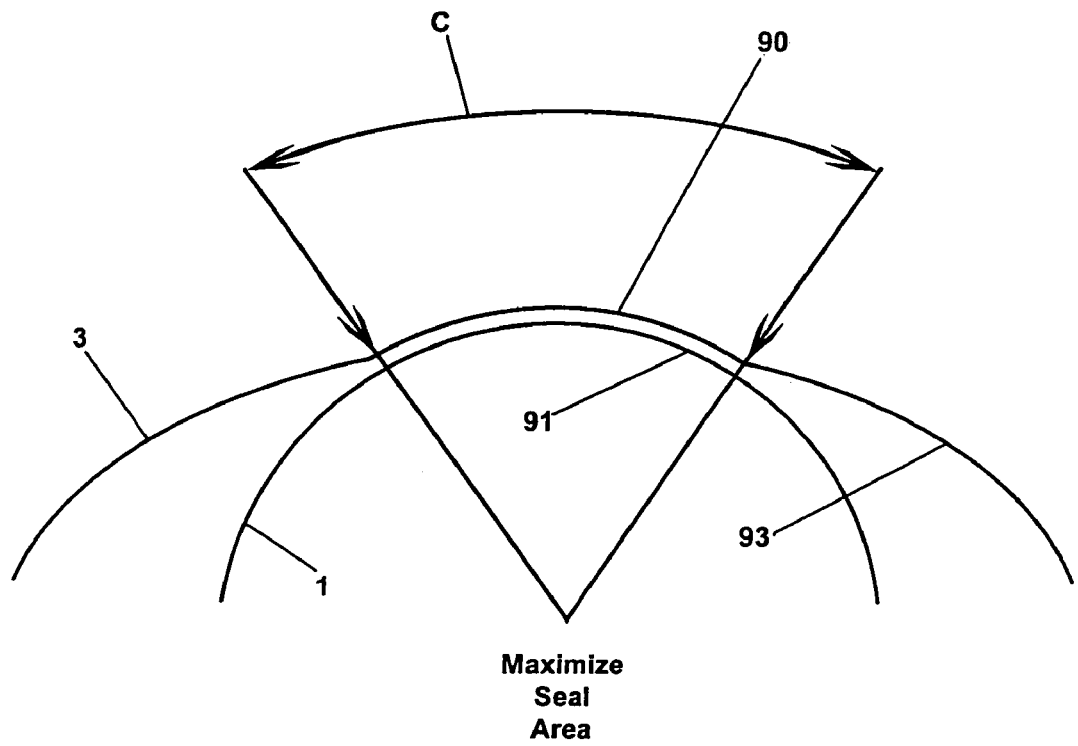

The next portion of the description is directed to the spindle 1 and vanes 2 which are detailed in FIGS. 4, 4A, 4B and 4C. The spindle 1 is an elongated cylinder body that includes a pair of diametrically disposed stub shafts 61 and 63 made from a non-magnetic stainless steel material, such as 316 SST and that is eccentrically mounted inside cylinder 3. Spindle 1 includes four axial slots 80 circumferentially spaced and off-set from the spindle center line. As noted in FIG. 4B the vanes made from a plastic material such as VESPEL ®, which is a polymer of amide made by DuPont de Nemours and Company, are mounted in slots 80 for reciprocal motion and rotate within cylinder 3 to generate power in the well known vane motor manner. However, this spindle differs from prior art spindles not only because of the off-set of slots 80 but it is slotted to increase the power thereof. To this end, as seen in FIGS. 4, 4A and 4B a series of cut out are introduced to spindle 1. The three axial grooves 82 adjacent to the working face of each of the vanes 2 increase the working area of the vane's working surface. As seen in FIG. 4B the arrows A represent the pressurized air impinging on the working or power face 83 of the vane 2. Additionally, circumferentially spaced slots 84 are formed in the peripheral surface of spindle 1 and serve as a shoulder where the inlet pressurized air impinges on the power face 85 to also, increase the power of the spindle and hence, the overall power of the surgical motor.

As mentioned above the slots 80 are off-set from the spindle center line CL. This serves to reduce the friction on the vanes as they return into the slots after the power cycle of the vanes. Since the spindle is rotating at approximately 80,000 RPM it creates a significant centrifugal force which tends to have its line of action toward the center line. The offset reduces the effect of the centrifugal force and significantly reduces the force that the vane needs to overcome when it reciprocates back into the slot 80.

Power generated by the vane motor is further increased by increasing the vane displacement by locating the discharge port further away from the inlet port. As noted in FIG. 4C the displacement between the inlet hole spans almost 180 degrees. In heretofore vane motors the span is closer. This is due to the fact that the inlets are now drilled holes and lesser number of discharge holes span a column of holes.

One of the problems inherent in heretofore known vane motors is that the point of contact or pinch point at the juncture where the spindle is tangent to the cylinder, the contact is simply a point. According to this invention the inner surface of cylinder 3 is undercoat as shown by the undercut 90 which defines an extended gap rather than a simple point. This extended gap serves as a seal, as does the pinch point in previous designs, however, the circumferential length of the gap is much longer such that the leakage is thwarted and hence, the seal is now more effective and the leakage is thusly reduced.

Figure 4E:
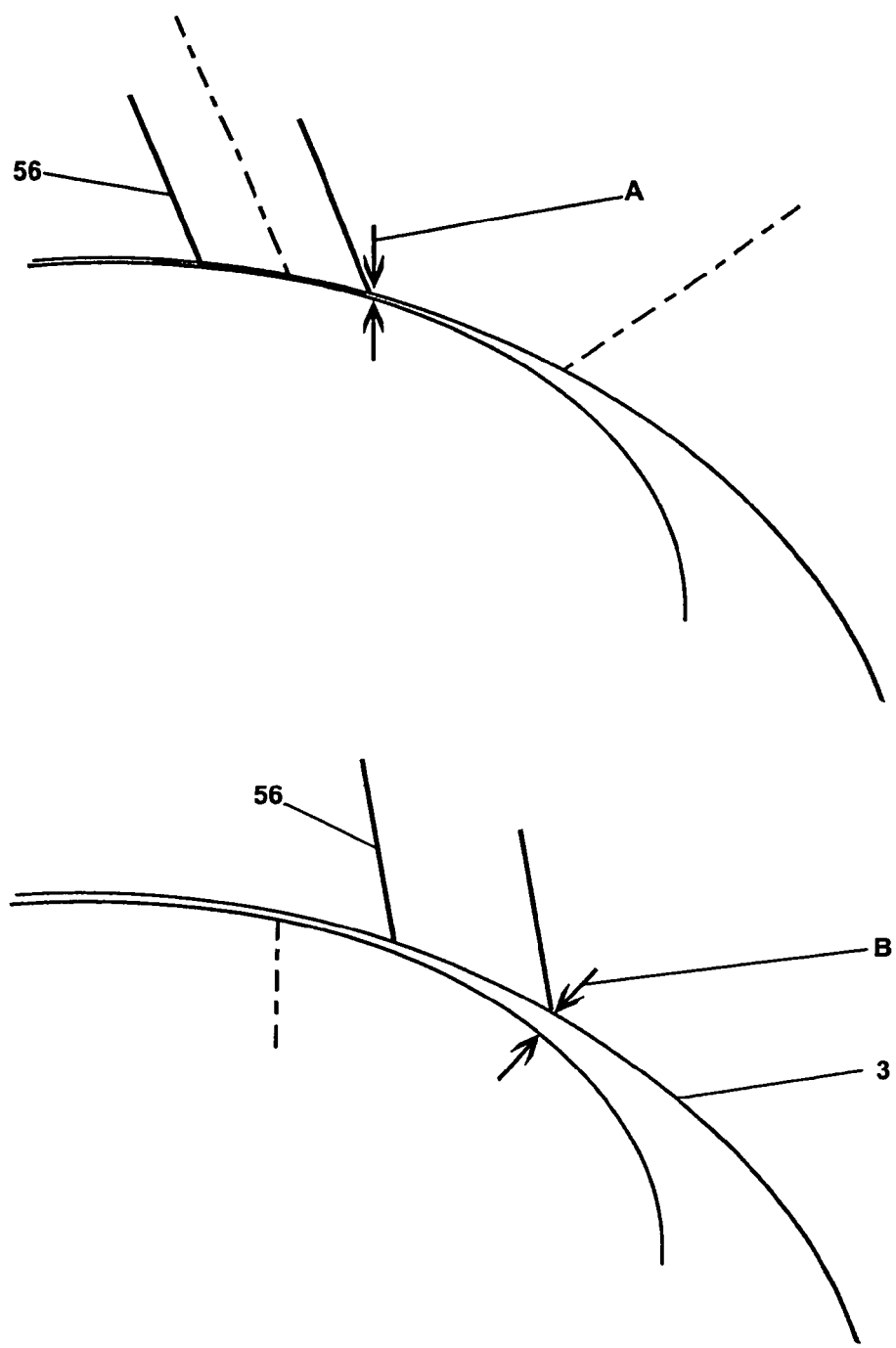
FIG. 4E is a view identical to the view in FIG. 4C illustrating the relationship of the inlet port of the cylinder to the vane of the spindle to increase the power of the motor.

Additional power is generated in accordance with this invention by judiciously orienting the inlet holes 56 further away from the pinch point in proximity to the working face of the vanes 2. As shown in FIG. 4E in hertofore designs the location of the air inlet hole is where the surfaces of the spindle and cylinder are close to the pinch point and the space between these surfaces is minimal compared to re-locating the holes 56 further away from the pinch point. Arrows A and B illustrate this feature. Obviously, the distance of the arrows A are closer to each other in comparison to the distance between the arrows B. The increase flow to the vane working surface adds to the power generated by the spindle.

In this motor the housing 30 encasing the components of the motor is made from a non-magnetic material such as commercially available 316 or 317 stainless steel. All the other metallic parts are likewise made from the same material. For example the spindle 1 is supported on either end by needle bearings 8 and 9 mounted in the pin retainers 10 which are alternately made up with 316 stainless steel pins or needles and commercially available Torlon pins or needles. These bearings are described in U.S. patent application Ser. No. 10/306,256, supra and for further details thereof reference should be made to this patent application which is incorporated herein by reference. Needle bearings 8 and 9 are circumferentially stacked in the back plate bearing 23 and the bearing housing 5 each of which include a cavity for holding grease. These cavities and bearings are suitably sealed.

The wear of the seal in steel housing 11 is reduced by axially stacking a plurality of seal discs 131 preferably made from Teflon material. Since the end seal discs are adjacent to non moving parts, they will have a tendency not to rotate. The discs in-between, however, will randomly rotate by virtue of the rotating shaft. Since each disc rotates at a different speed the seals will exhibit less wear and hence, contribute to the long life of the motor as well as effectively providing an improved seal for sealing the grease in the bearing housing.

The thrust generated by the surgical motor when the surgical procedure is being performed is taken up by the thrust washer 6 suitably made from commercially available Delrin AF and the ball 29 suitably made from a commercially available ceramic material. The ball 29 is located in coincidence with the center line of the motor so that it doesn't rotate. This assures that the wear thereof is minimal and it doesn't generate heat. As noted in FIG. 1 the thrust washers 6 sandwich the spindle 1 so that all the thrust loads are taken up by the thrust ball 29 and thrust washers 6. By virtue of this design the only loads that are seen by the needle bearings are the radial loads.

The outer surface 94 of the housing 30 is serrated or threaded and lies underneath an outer sleeve made from a suitable plastic material. Since this is the location where the surgeon holds onto the surgical motor when performing a surgical procedure such as burring or drilling, the serrations or threads and the material selected maintain a tolerable temperature for ease of handling this instrument.

Power is transmitted to the chuck for driving the cutter and the like by the spindle extension 14 which connects at one end 120 to the spindle and includes the diametrically drilled holes 122 that receive a pin for connecting to the chuck assembly. The central bore 124 on the right hand end of the spindle extension 14 is adapted to receive the end of the cutter shaft (not shown) where the retaining balls 19 (FIG. 2) fit into the holes 126 for locking the cutter to the spindle extension 14 and chuck for rotating the same.

While the bearing adjustment screw 24 locks the back plate bearing 23 to secure the spindle and cylinder in the motor housing (FIG. 1) the motor adapter mounted on the end of the motor housing (left hand side as viewed in FIG. 1) the motor adapter 27 serves as a manifold to direct the air into and out of the motor. The motor adapter 27 includes an inlet port 100 and discharge grooves 102 that are connected to the hose 107 that, in turn, is connected to the source of high pressure and the discharge receiver.

Figure 7:
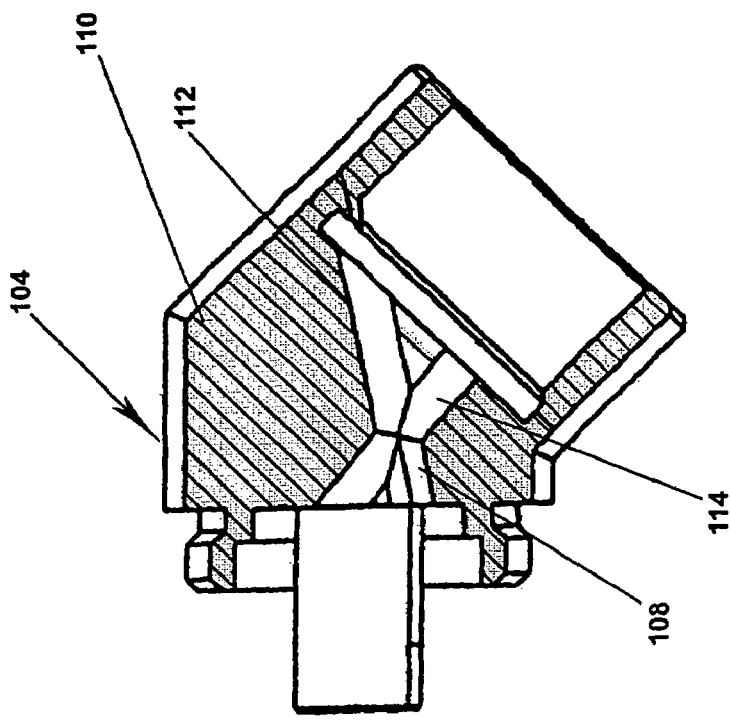
FIG. 7 is a sectional view of the same component depicted in FIG. 6 illustrating another view of the universal swivel.
Figure 6:
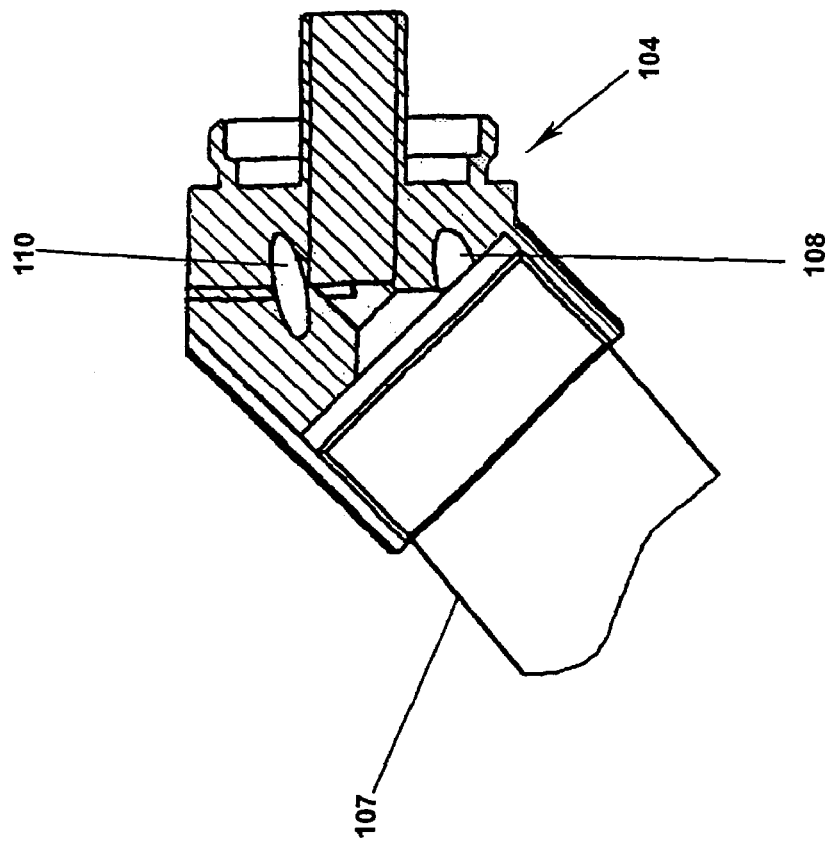
FIG. 6 is a sectional view of the universal swivel that is mounted to the hose connection for feeding and discharging the vane motor's compressed air of this invention.
Figure 8:
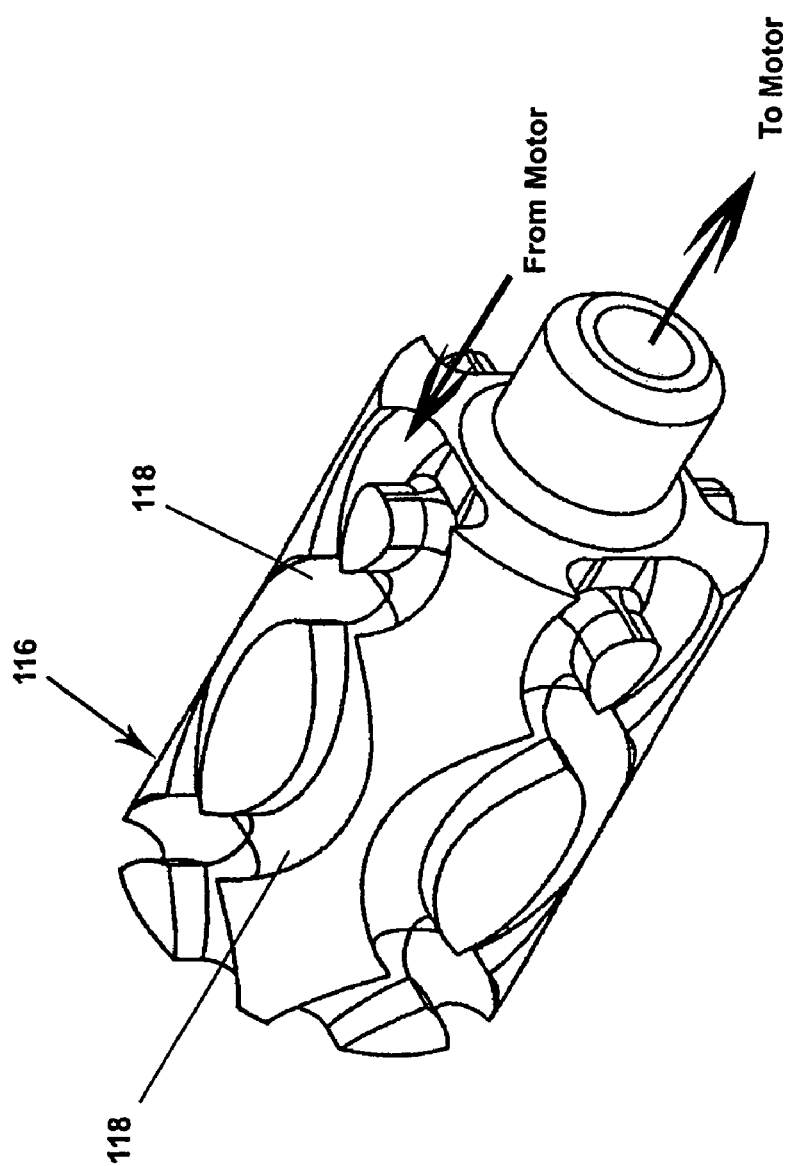
FIG. 8 is a perspective view of the inlet flow divider for crisscrossing the outlet air flowing out of the motor depicted in FIGS. 1 and 2.
Figure 9:
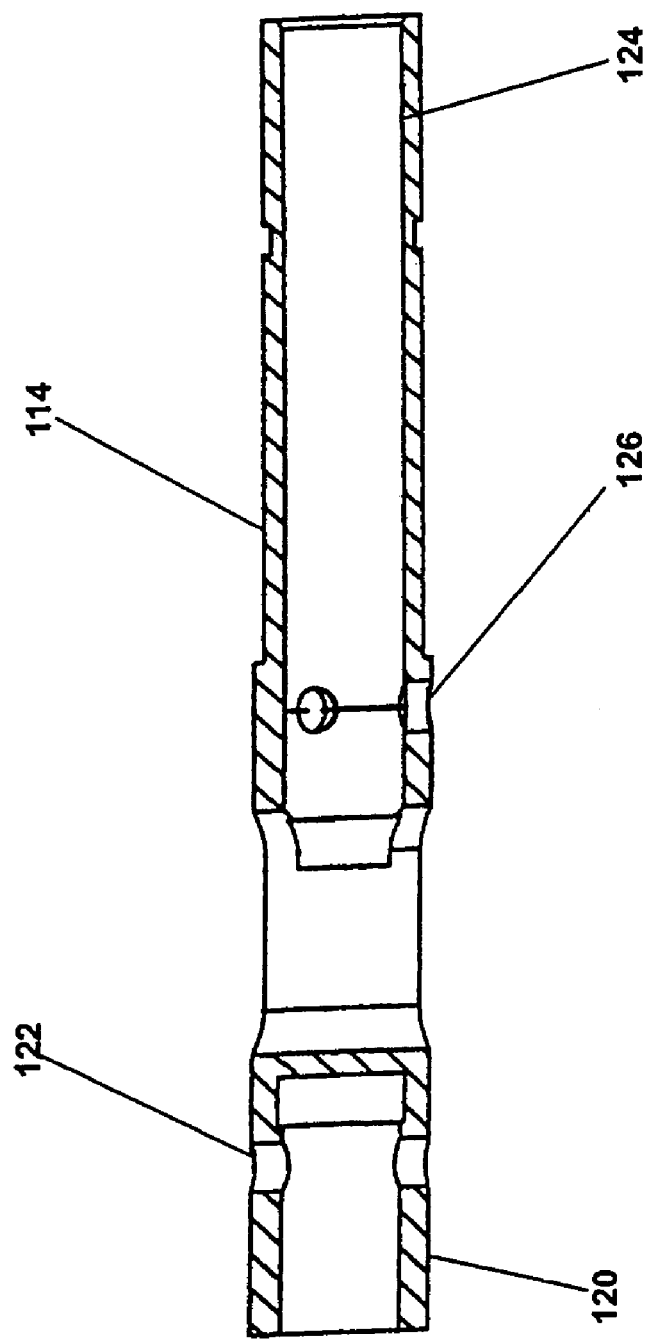
FIG. 9 is a plan view of the spindle extension in the motor of FIGS. 1 and 2.

While the hose 107 for the heretofore known surgical motors are well known, in accordance with this invention the hose is modified to reduce the noise level created by the flow of the high pressure air. To this end as seen in FIGS. 6 and 7, the universal swivel 104 mounted at the end of the hose and fitted into the inlet port of the motor adapter 27 is designed with cross-over holes 108, 110, 112 and 114, that flows the air in a crisscross pattern to cancel the noise generated by the flowing discharge air. A cylindrically shaped flow divider 116 (FIG. 8) is mounted in the inlet passage of the hose (not shown) and includes a plurality of cross over passages 118 so that the air that flows out of the motor is in a crisscross pattern. Like the flow passages in the universal adapter, the flow passages in the flow divider 116 attenuates the noise that is otherwise created by the high velocity outlet air.

This surgical motor is particularly efficacious for use in proximity to an MRI motor as noted above, but it also can be used in an environment that doesn't include the MRI machine. However, since this motor includes features that increase power, reduce wear, suppress noise and has an increase life, the concepts included in this motor has utility with other surgical instruments and can also be modified with different materials to reduce the cost of the motor. Additionally, this motor operates almost lubrication free. While the bearing housings include sealed grease compartments, unlike the heretofore motors that operate with an air/oil mist in the motor operating fluid, this motor does not require this condition. Hence, during normal operations, the compressed air driving the vane motor is oil free. It is mentioned that the motor is pre-treated by an air/oil mist that flows into the motor before being used by the surgeon. The normal sequence of operation is that after the motor has been used in a surgical procedure, the motor is throughly cleansed, the motor is connected on line where an air/oil mist is flown therein until the operator feels that the motor has reached its operating speed. The air/mist is then shut down and the motor is sterilized by any well known means such as by autoclave.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. A pneumatic surgical motor(50) having a housing (30), a sleeve (40) made from a plastic material and being substantially coextensive and contiguous with said housing (30) surrounding said housing (30) and being sufficiently small in diameter to serve as a handle for the surgeon, said housing having a plurality of serrations formed on the periphery thereof and extending axially and defining a handle for the operator, the apex of the serrations engaging the inner surface of said housing (30) and the valley portion defining an air gap acting as an insulator for said sleeve (40), and being sufficiently small in diameter to accommodate a cylindrical handle for the surgeon to grab to use said motor (50), a vane motor (5 3)including a spindle (I) being made from a non-magnetic stainless steel material and being rotary supported in said housing (30), said spindle (1) being supported by bearings (5) and attachment mechanism (52) affixed to said housing (30) for receiving surgical tools being powered by said vane motor (53), passageways (58,62) in said housing (30) for leading pressurized air into said housing (30) and into said vane motor (53) for rotating said spindle (1), and discharge aperture (55) in said vane motor (53)for leading spent air out of said housing (30), and a portion of said air passing over said bearings (5) for cooling said bearings (5) before being admitted into said vane motor (53), a cylinder (3), said spindle (1) being rotary supported in said cylinder (3), said spindle (1) having diametrically opposing stub shafts (61,63) being supported by bearings (5), said spindle having an outer surface (91) and said cylinder having an inner surface (93), said spindle (1) and said cylinder (2) being eccentrically mounted so that the spindle (1) comes into contact with the cylinder (3) at the pinch point defining a sealing area, means for increasing the sealing area by undercutting said inner surface (93) of said cylinder to contour said inner surface (93) for redefining said pinch point into a crescent shaped seal.

2. A pneumatic surgical motor (50) having a housing (30) as claimed in claim 1 wherein said vane motor (53) includes a spindle (1) having stub shafts (61,63) and vanes (2) being rotary supported in said cylinder (3), said spindle (1) being supported by needle bearings (8,9), said needle bearings having a plurality of circumferentially mounted needles, alternate needles (8) being made from a metallic material and alternate needles (9) being made from a plastic material.

3. A pneumatic surgical motor (50)having a housing (30) as claimed in claim 2 including a hose (107) attached to said surgical motor (50) for leading pressurized air into passageways (58,62) in said housing (30) and into said vane motor (53) for rotating said spindle (1), and discharge aperture (55) in said vane motor (53)for leading spent air out of said housing (30) into said hose, and a flow divider (116) mounted in said hose (107) and having cross over passages for flowing the spent air in a cris-cross pattern for noise reduction.

4. A pneumatic surgical motor (50) having a housing (30) as claimed in claim 3 including seal means (11) surrounding said fore stub shaft (63), said seal means including a plurality of axially stacked circular discs 131 made from a plastic material, the end discs being compacted by stationary parts in said housing (30)and the inner discs (131) being rotating by the fore stub for enhancing wear on said disc.

5. A pneumatic surgical motor (50) having a housing (30) as claimed in claim 4 wherein said spindle (1) includes an outer surface (91) and said cylinder having an inner surface (93), said spindle (1) and said cylinder (2) being eccentrically mounted so that the spindle (1) comes into contact with the cylinder (3) at the pinch point, positioning said inlet hole (56) downstream of said pinch point.

6. In combination, a pneumatic surgical motor (50) having a housing (30), a vane motor (53) comprising a cylinder (3), a spindle (1) having vanes (2) adapted to be rotated in said cylinder (3) by pressurized air, an attachment (52)affixed to said housing for receiving surgical tools being powered by said vane motor (53), a first plurality of axially spaced inlet holes (56) substantially spanning the length of said cylinder (3), an axial groove (58) formed in said cylinder (3) adjacent to said first plurality of axially spaced inlet holes (56), an enclosed portion (69) partially extending axially from the aft end towards the fore end of the cylinder (3) for blocking out the air in said axial slot from entering said first plurality of axially spaced inlet holes (56), a plurality of partially circumferential axially spaced grooves (60) in said cylinder (3), a second axial groove (62) circumferentially spaced from said axial groove (58) and extending the length of the cylinder and being exposed to said first plurality of axially space inlet holes 56, a second plurality of axially and circumferentially spaced discharge holes (66) formed in said cylinder (3) spaced on the opposite side of said cylinder (3) relative to first plurality of axially spaced inlet holes (56), whereby the pressurized air is admitted at the aft end of the surgical motor (50) into passage (58) flows toward the fore end thereof and around said cylinder (3) and into said plurality of axially spaced inlet holes (56) while a portion of said pressurized air flows into said circumferential grooves (60) and into a portion of said plurality of axially spaced inlet holes (56) for powering said spindle (1) and discharging through said plurality of axially and circumferentially spaced discharge holes (66), a hose (107) attached to said surgical motor (50) for leading pressurized air into passageways(58,62) in said housing (30) and into said vane motor (53) for rotating said spindle(1), and discharge aperture (55) in said vane motor (53) for leading spent air out of said housing (30), and a flow divider (116) mounted in said hose (107) and having cross over passages for flowing the pressurized air in a cris-cross pattern for noise reduction 7. In combination as claimed in claim 6 including a vane (2) affixed to said spindle (1), said vane (2) rotates and slides over each of the inlet holes (56) and discharge holes (66) in said cylinder (3), and said discharge holes (66) are arranged in a predetermined pattern wherein the vane (2) contacts the inner surface of said cylinder (3) uniformly relative to the amount of surface of said cylinder (3) being touched by said vane (2) throughout the cycle of the vane's (2) rotation.

8. In combination as claimed in claim 7 wherein said spindle (1)has an outer surface (91) and said cylinder (3) having an inner surface (93), said spindle (1) and said cylinder (2) being eccentrically mounted so that the spindle (1) comes into contact with the cylinder (3) at the pinch point defining a sealing area, means for increasing the sealing area by undercutting said inner surface (93) of said cylinder to contour said inner surface (93) for redefining said pinch point.

9. In combination as claimed in claim 8 wherein said spindle (1) being supported by needle bearings (8,9), said needle bearings having a plurality of circumferentially mounted needles, alternate needles (8) being made from a stainless steel material and alternate needles (9) being made from a plastic material.

10. In combination as claimed in claim 9 said spindle (I) having fore and aft stub shafts (61,63) being supported by bearings (5), seal means (11) surrounding said fore stub shaft (63), said seal means including a plurality of axially stacked circular discs 131 made from a plastic material, the end discs being compacted by stationary parts in said housing (30)and the inner discs (131) being rotating by the fore stub for enhancing wear on said disc.

11. A pneumatic surgical motor (50)having a housing (30), a sleeve (40) substantially coextensive and contiguous with said housing (30) surrounding said housing (30) defining a handle, said housing having a plurality of serrations formed on the periphery thereof and extending axially and defining a handle for the operator, the apex of the serrations engaging the inner surface of said housing (30) and the valley portion defining an air gap acting as an insulator for said sleeve (40), a vane motor (53)including a spindle (1) supporting four vanes and cylinder (3) being rotatably supported in said cylinder (3), said spindle (1) having fore stub shaft 61 and aft stub shaft (63) being supported by bearings (5), an attachment mechanism (52) affixed to said housing (30) for receiving surgical tools being powered by said vane motor (53), passageways (58,62) in said housing (30) for leading pressurized air into said housing (30)and into said vane motor (53) for rotating said spindle (1), and discharge aperture (55) in said vane motor (53) for leading spent air out of said housing (30), and a portion of said air passing over said bearings (5) for cooling said bearings (5) before being admitted into said vane motor (53), said spindle (1) includes four circumferentially spaced axial slots (80) formed adjacent to each of said vanes (2) for enhancing the power of said spindle (1) each slot being eccentrically mounted relative to the center of said spindle (1) for carrying each of said four vanes and a plurality axially spaced undercuts formed adjacent to each of said axial slots (80).

12. A pneumatic surgical motor (50) as claimed in claim 11 wherein said spindle has an outer surface (91) and said cylinder has an inner surface (93), said spindle (1) and said cylinder (2) being eccentrically mounted so that the spindle (1) comes into contact with the cylinder (3) at the pinch point defining a sealing area, means for increasing the sealing area by undercutting said inner surface (93) of said cylinder to contour said inner surface (93) for redefining said pinch point.

13. A pneumatic surgical motor (50) as claimed in claim 11 wherein said spindle (1) being supported by needle bearings (8,9), said needle bearings having a plurality of circumferentially mounted needles, alternate needles (8) being made from a non-magnetic stainless steel material and alternate needles (9) being made from a plastic material.

14. A pneumatic surgical motor (50) as claimed in claim 11 including a hose (107) attached to said surgical motor (50) for leading pressurized air into passageways (58,62) in said housing (30) and into said vane motor (53) for rotating said spindle (1), and discharge aperture (55) in said vane motor (53) for leading spent air out of said housing (30), and a flow divider (116) mounted in said hose (107) and having cross over passages for flowing the pressurized air in a cris-cross pattern for noise reduction.

15. A pneumatic surgical motor (50) as claimed in claim 11 wherein said spindle having an outer surface (91) and said cylinder having an inner surface (93), said spindle (1) and said cylinder (2) being eccentrically mounted so that the spindle (1) comes into contact with the cylinder (3) at the pinch point, positioning said inlet hole (56) downstream of said pinch point 16. A pneumatic surgical motor (50) having a housing (30), a sleeve (40) substantially coextensive and contiguous with said housing 30 surrounding said housing 30) defining handle. said housing having a plurality of serrations formed on the periphery thereof and extending axially and defining a handle for the operator, the apex of the serrations engaging the inner surface of said housing (30) and the valley portion defining an air gap acting as an insulator for said sleeve (40). a vane motor (53)including a spindle (1) supporting four vanes and cylinder (3) being rotatably supported in said cylinder (3), said spindle (1) having fore stub shaft (61) and aft stub shaft (63) being supported by bearings (5), an attachment mechanism (52) affixed to said housing (30) for receiving surgical tools being powered by said vane motor (53), passageways (58,62) in said housing (30) for leading pressurized air into said housing (30) and into said vane motor (53) for rotating said spindle (1), and discharge aperture (55) in said vane motor (53) for leading spent air out of said housing (30), and a portion of said air passing over said bearings (5) for cooling said bearings (5) before being admitted into said vane motor (53), said spindle (1) includes four circumferentially spaced axial slots (80) formed adjacent to each of said vanes (2) for enhancing the power of said spindle (1) each slot being eccentrically mounted relative to the center of said spindle (1) for carrying each of said four vanes and a plurality axially spaced undercuts formed adjacent to each of said axial slots (80), seal means (11) surrounding said fore stub shaft (63), said seal means including a plurality of axially stacked circular discs (131) made from a plastic material, the end discs being compacted by stationary parts in said housing (30)and the inner discs (131) being rotating by the fore stub for enhancing wear on said disc.

17. A pneumatic surgical motor (50) having a housing (30) being serrated at the outer periphery thereof, a sleeve surrounding said serrations at the outer periphery for defining a handle, a vane motor (53) in said housing, said vane motor and a chuck (52) affixed to said housing for receiving surgical tools being powered by said vane motor (53), said vane motor (53) having a cylinder (3), a spindle(1) and being rotary supported in said cylinder (3) and vanes (2) slidably mounted in said spindle (1), a first plurality of axially spaced inlet holes (56) substantially spanning the length of said cylinder (3), an axial groove (58) formed in said cylinder (3) adjacent to said first plurality of axially spaced inlet holes (56), an enclosed portion (69) partially extending axially from the aft end to the fore end of the cylinder (3) for blocking out the air in said axial slot from entering said first plurality of axially spaced inlet holes (56), a plurality of partially circumferential axially spaced grooves (60) in said cylinder (3), a second axial groove (62) circumferentially spaced from said axial groove (58) and extending the length of the cylinder and exposing said first plurality of axially space inlet holes (56), a second plurality of axially and circumferentially spaced discharge holes (66) formed in said cylinder (3) spaced on the opposite side of said cylinder (3) relative to first plurality of axially spaced inlet holes (56), whereby the pressurized air is admitted at the aft end of the surgical motor (50) into passage (58) flows toward the fore end thereof and around said cylinder (3) and into said plurality of axially spaced inlet holes (56) while a portion of said pressurized air flows into said circumferential grooves (60) and into a portion of said plurality of axially spaced inlet holes (56) for powering said spindle (1) and discharging through said plurality of axially and circumferentially spaced discharge holes (66), at least one vane (2) being rotatably mounted in said cylinder, said vane having a curved bottom portion and a straight top portion and said bottom portion being slidably mounted in an axial slot (80) formed in said cylinder (3), said vane (2) having a power face where the pressurized air impinges, an undercut (82) formed adjacent to said power face of said vane (2) for increasing the area of the power face where the air impinges thereon to enhance power of the spindle (1).

18. The combination of claim 17 including at least one slot formed in the outer periphery of said spindle having a power face for the air to impinge thereon to enhance the power of said spindle (1).

19. The combination of claim 18 wherein said spindle (1) includes four circumferentially spaced axial slots (80) each slot being eccentrically mounted relative to the center of said spindle (1).

20. The combination of claim 19 wherein each of said four axial slots (80) includes a plurality axially spaced undercuts formed adjacent to each of said axial slots (80).

21. The combination of claim 20 including four circumferentially spaced slots (84) formed adjacent to each of said vanes (2) for enhancing the power of said spindle (1).

22. The combination of claim 21 wherein said plurality of axially spaced inlet holes (56) are cylindrical in shape.

23. The combination of claim 22 wherein said vane (2) rotates and slides over each of the inlet holes (56) and discharge holes (66) in said cylinder (3) and said discharge holes (66) are arranged in a predetermined pattern wherein the vane (2) contacts of the inner surface of said cylinder (3) will be uniform relative to the amount of surface of said cylinder (3) being touched by said vane (2) throughout the cycle of the vane's rotation.

24. In combination, a pneumatic surgical motor (50) having a housing (30) being serrated at the outer periphery thereof, a sleeve surrounding said serrations at the outer periphery for defining a handle, a vane motor (53) in said housing, said vane motor and a chuck (52) affixed to said housing for receiving surgical tools being powered by said vane motor (53), said vane motor (53) having a cylinder (3), a spindle (1) being rotary supported in said cylinder (3) and four vanes (2) slidably mounted in said spindle (1), a first plurality of axially spaced inlet holes (56) substantially spanning the length of said cylinder (3), an axial groove (58) formed in said cylinder (3) adjacent to said first plurality of axially spaced inlet holes (56), an enclosed portion (69) partially extending axially from the aft end to the fore end of the cylinder (3) for blocking out the air in said axial slot from entering said first plurality of axially spaced inlet holes (56), a plurality of partially circumferential axially spaced grooves (60) in said cylinder (3), a second axial groove (62) circumferentially spaced from said axial groove (58) and extending the length of the cylinder and exposing said first plurality of axially space inlet holes (56), a second plurality of axially and circumferentially spaced discharge holes (66) formed in said cylinder (3) spaced on the opposite side of said cylinder (3) relative to first plurality of axially spaced inlet holes (56), whereby the pressurized air is admitted at the aft end of the surgical motor (50) into passage (58) flows toward the fore end thereof and around said cylinder (3) and into said plurality of axially spaced inlet holes (56) while a portion of said pressurized air flows into said circumferential grooves (60) and into a portion of said plurality of axially spaced inlet holes (56) for powering said spindle (1) and discharging through said plurality of axially and circumferentially spaced discharge holes (66), at least one vane (2) being rotatably mounted in said cylinder, said vane having a curved bottom portion and a straight top portion and said bottom portion being slidably mounted in an axial slot (80) formed in said cylinder (3), said vane (2) having a power face where the pressurized air impinges, an undercut (82) formed adjacent to said power face of said vane (2) for increasing the area of the power face where the air impinges thereon to enhance power of the spindle (1), said spindle (1) includes four circumferentially spaced axial slots (80) each slot being eccentrically mounted relative to the center of said spindle (1), each of said four axial slots (80) includes a plurality axially spaced undercuts formed adjacent to each of said axial slots (80), four circumferentially spaced slots (84) formed adjacent to each of said vanes (2) for enhancing the power of said spindle (1), said spindle has an outer surface (91) and said cylinder has an inner surface (93), said spindle (1) and said cylinder (2) being eccentrically mounted so that the spindle (1) comes into contact with the cylinder (3) at the pinch point defining a sealing area, means for increasing the sealing area by undercutting said inner surface (93) of said cylinder to contour said inner surface (93) for redefining said pinch point, said spindle (1) being supported by needle bearings (8,9), said needle bearings having a plurality of circumferentially mounted needles, alternate needles (8) being made from a metallic material and alternate needles (9) being made from a plastic material, a hose (107) attached to said surgical motor (50) for leading pressurized air into passageways (58,62) in said housing (30) and into said vane motor (53) for rotating said spindle (1), and discharge aperture (55) in said vane motor (53) for leading spent air out of said housing (30), and a flow divider (116) mounted in said hose (107) and having cross over passages for flowing the pressurized air in a cris-cross pattern for noise reduction.

25. The combination of claim 24 including at least one slot formed in the outer periphery of said spindle having a power face for the air to impinge thereon to enhance the power of said spindle (1).

26. The combination of claim 25 wherein said spindle (1) includes four circumferentially spaced axial slots (80) each slot being eccentrically mounted relative to the center of said spindle (1).

27. The combination of claim 26 wherein each of said four axial slots (80) includes a plurality axially spaced undercuts formed adjacent to each of said axial slots (80).

28. The combination of claim 27 including four circumferentially spaced slots (84) formed between each of said vanes (2) for enhancing the power of said spindle (1).

* * * * *